(12) United States Patent
Inamura et al.

(10) Patent No.: US 8,894,948 B2
(45) Date of Patent: Nov. 25, 2014

(54) CLEANING DEVICE, METHOD FOR DETECTING SUCTION NOZZLE CLOGGING, AND AUTOMATIC ANALYZER

(75) Inventors: Shinichi Inamura, Shizuoka-ken (JP); Kenichi Kakizaki, Mishima (JP); Satoshi Nemoto, Mishima (JP)

(73) Assignee: Beckman Coulter, Inc., Brea, CA (US)

( * ) Notice: Subject to any disclaimer, the term of this patent is extended or adjusted under 35 U.S.C. 154(b) by 37 days.

(21) Appl. No.: 12/641,193

(22) Filed: Dec. 17, 2009

(65) Prior Publication Data

US 2010/0098590 A1 Apr. 22, 2010

Related U.S. Application Data

(63) Continuation of application No. PCT/JP2007/063032, filed on Jun. 28, 2007.

(51) Int. Cl.
*B01L 3/02* (2006.01)
*G01N 35/10* (2006.01)
*B01L 99/00* (2010.01)

(52) U.S. Cl.
CPC ............ *G01N 35/1016* (2013.01); *B01L 99/00* (2013.01); *B01L 2200/143* (2013.01); *G01N 2035/1018* (2013.01); *G01N 35/1004* (2013.01)
USPC .......................................... 422/510; 422/509

(58) Field of Classification Search
CPC ........................... B01L 2200/143; G01N 1/34
USPC ................. 422/510, 82.05, 105, 110
See application file for complete search history.

(56) References Cited

U.S. PATENT DOCUMENTS 5,357,117 A 10/1994 Hayashi et al.
6,267,927 B1 * 7/2001 Pomar Longedo et al. ...... 422/65

FOREIGN PATENT DOCUMENTS

| JP | 05-317683 A | 12/1993 |
|---|---|---|
| JP | 06-230014 A | 8/1994 |
| JP | 06-249862 A | 9/1994 |
| JP | 06-265558 A | 9/1994 |
| JP | 2000-266763 A | 9/2000 |

OTHER PUBLICATIONS

International Search Report from PCT/JP2007/063032, mailed Aug. 7, 2007 (3 pages, includes English Translation).
Supplementary European Search Report and Search Opinion from EP 07767825.8, dated Mar. 13, 2013 (9 pages).

* cited by examiner

*Primary Examiner* — Natalia Levkovich
(74) *Attorney, Agent, or Firm* — Kilpatrick Townsend & Stockton LLP

(57) ABSTRACT

A cleaning device includes a discharge nozzle that discharges cleaning liquid; a suction nozzle that sucks the cleaning liquid or reaction liquid in the cleaning tank or the reaction vessel; a discard vessel connected to the suction nozzle via a pipe to discard the cleaning liquid or the reaction liquid; a detecting unit that detects whether an electrostatic capacity at least between the suction nozzle and an electrode provided in the pipe exceeds a threshold value; a determination unit that determines that the suction nozzle is clogged when a totalizing time, for which the electrostatic capacity exceeds the threshold value during a preset clogging determination time, is longer than a totalizing time, for which the electrostatic capacity exceeds the threshold value during a preset normal determination time; and a control unit that stops the discharge nozzle from discharging the cleaning liquid to the reaction vessel when the suction nozzle is clogged.

20 Claims, 11 Drawing Sheets

CLEANING DEVICE, METHOD FOR DETECTING SUCTION NOZZLE CLOGGING, AND AUTOMATIC ANALYZER

CROSS-REFERENCE TO RELATED APPLICATIONS

This application is a continuation of PCT international application Ser. No. PCT/JP2007/063032 filed on Jun. 28, 2007 which designates the United States, incorporated herein by reference.

BACKGROUND OF THE INVENTION

1. Field of the Invention

The present invention relates to a cleaning device, a method for detecting suction nozzle clogging, and an automatic analyzer.

2. Description of the Related Art

A conventional automatic analyzer includes a cleaning device that sucks reaction liquid, which is obtained through a reaction between a specimen and a reagent, from a reaction vessel and discharges cleaning liquid into the reaction vessel to clean the reaction vessel (for example, see Japanese Patent Application Laid-open No. 2000-266763). In such an automatic analyzer, the cleaning device sucks the reaction liquid from the reaction vessel using a nozzle, and sometimes a foreign material in the reaction liquid clogs the nozzle.

SUMMARY OF THE INVENTION

A cleaning device according to an aspect of the present invention includes a discharge nozzle that discharges cleaning liquid; a suction nozzle that is inserted into a cleaning tank or a reaction vessel along with the discharge nozzle to suck the cleaning liquid or reaction liquid in the cleaning tank or the reaction vessel; a discard vessel that is connected to the suction nozzle via a pipe to discard the cleaning liquid or the reaction liquid; a detecting unit that detects whether an electrostatic capacity at least between the suction nozzle and an electrode provided in a middle of the pipe exceeds a predetermined threshold value; a determination unit that determines that the suction nozzle is clogged when a totalizing time, for which the electrostatic capacity exceeds the predetermined threshold value during a preset clogging determination time, is longer than a totalizing time, for which the electrostatic capacity exceeds the predetermined threshold value during a preset normal determination time; and a control unit that stops the discharge nozzle from discharging the cleaning liquid to the reaction vessel when the determination unit determines that the suction nozzle is clogged.

According to another aspect of the present invention, there is provided a method for detecting suction nozzle clogging in a cleaning device having a discharge nozzle that discharges cleaning liquid, a suction nozzle that is inserted into a cleaning tank or a reaction vessel along with the discharge nozzle to suck cleaning liquid or reaction liquid in the cleaning tank or the reaction vessel, and a discard vessel that is connected to the suction nozzle via a pipe to discard the cleaning liquid or the reaction liquid, the method including detecting whether an electrostatic capacity at least between the suction nozzle and an electrode provided in a middle of the pipe exceeds a predetermined threshold value; and determining that the suction nozzle is clogged when a totalizing time, for which the electrostatic capacity exceeds the predetermined threshold value during a preset clogging determination time, is longer than a totalizing time, for which the electrostatic capacity exceeds the predetermined threshold value during a preset normal determination time.

According to still another aspect of the present invention, there is provided an automatic analyzer that stirs a specimen and a reagent to cause a reaction, measures an optical characteristic of reaction liquid, and analyzes the reaction liquid, the automatic analyzer cleaning a suction nozzle that sucks cleaning liquid or the reaction liquid using the cleaning device The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
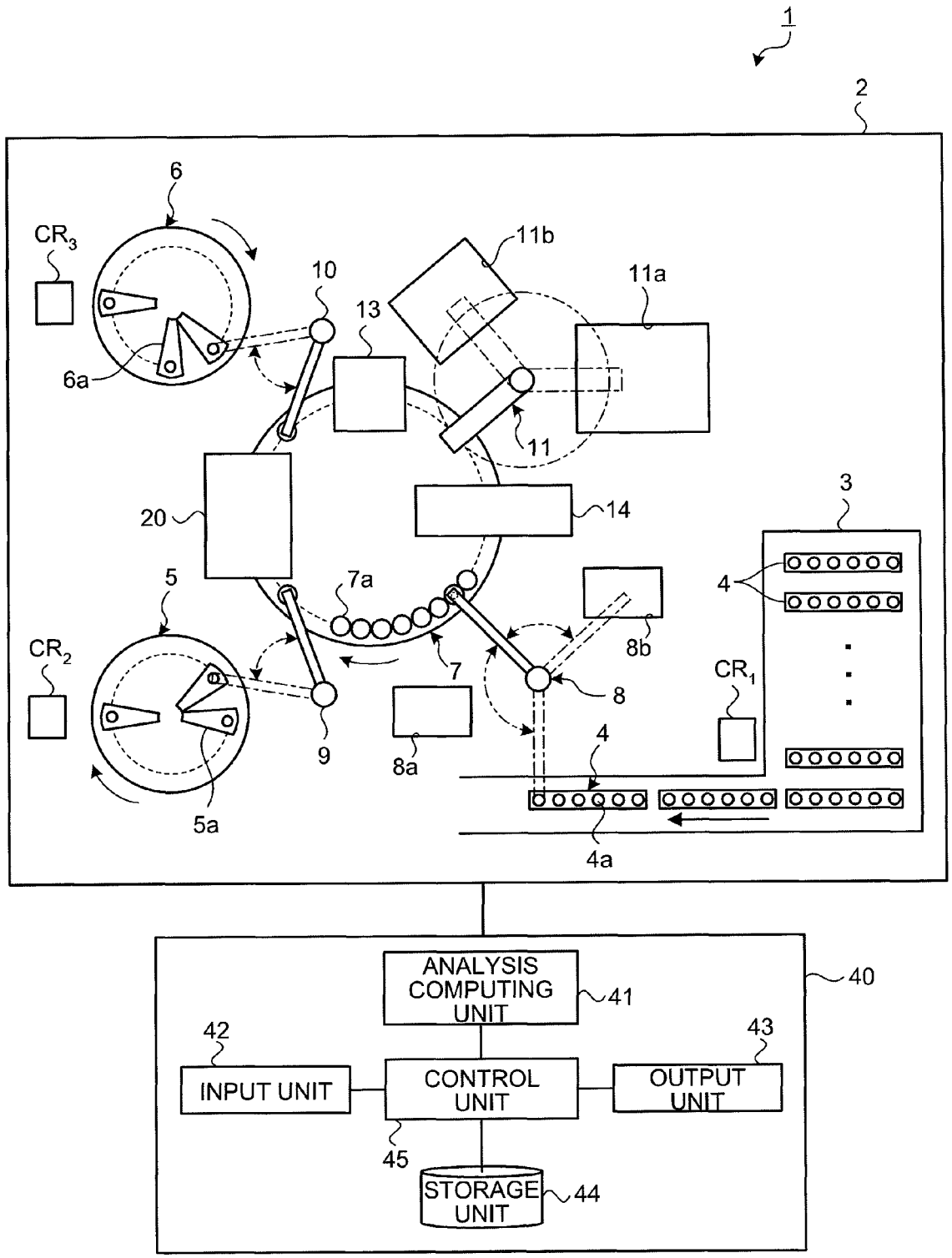
FIG. 1 is a schematic diagram illustrating the configuration of an automatic analyzer according to an embodiment of the present invention.

Exemplary embodiments of a cleaning device, a method for detecting suction nozzle clogging, and an automatic analyzer will be described below in detail with reference to the accompanying drawings. An automatic analyzer for immune analysis, to which the cleaning device and the method for detecting suction nozzle clogging are applied, will be described.

<Outline of Immune Analysis Process>

The outline of an immune analysis process performed by an automatic analyzer according to an embodiment of the present invention is described first. In the present embodiment, an immune measurement using a heterogeneous reaction is performed. As an example, a case of measuring the concentration of a predetermined antigen in a specimen using an enzyme immunoassay (EIA) will be explained. In the immune analysis process, an immune reaction (antigen-antibody reaction) is first caused by mixing a specimen and a solid phase that is sensitized by an antibody that specifically couples to a predetermined antigen in the specimen. In the following description, a reaction vessel is applied as a solid phase. It is assumed that a predetermined antibody is previously adsorbed in the vicinity of the inner-wall bottom surface of the reaction vessel.

After the immune reaction, reaction liquid within the reaction vessel is sucked by a suction nozzle, B/F cleaning of the reaction vessel (pre-B/F cleaning) is performed by predetermined B/F cleaning liquid discharged from a discharge nozzle, and then an antibody or a specimen component (including an antigen), which is not specifically coupled to the antibody and is isolated from the antibody, is separated and removed from the solid phase. Then, the suction nozzle moves to a cleaning tank along with the discharge nozzle to be cleaned. In the reaction vessel, chromogenic substrate, in which enzyme that is labeled substance shows activity, is added. A chromogenic reaction is caused between labeled substance remaining in the reaction vessel and the chromogenic substrate. A chromogenic amount is optically measured. Then, an antigen concentration in the specimen, which is an analysis target, is obtained by performing a comparison between data obtained by the measurement and data (calibration curve) obtained from a normal specimen of which the concentration of an antigen is known.

Sometimes, operations of the immune reaction, B/F cleaning, and nozzle cleaning are performed plural times. Similarly to the above, the concentration of a predetermined antibody in a specimen can be measured. In this case, an antigen that specifically couples to the antibody is previously adsorbed on a solid phase. An analysis of specimen can be performed by applying an immunoassay method using a heterogeneous reaction other than an enzyme immunoassay described above. Such an immunoassay method includes a fluorescent immunoassay (FIA) that uses a fluorescent substance as a labeled substance, a radioactive immunoassay (RIA) that uses a radioactive isotope as a labeled substance, a chemical enzyme immunoassay (CLIA) that uses a chemiluminescent substrate as a labeled substance, and a spin reagent immunoassay (SIA) that uses a spin reagent as a labeled substance.

<Configuration of Automatic Analyzer and Cleaning Device>

FIG. 1 is a schematic diagram illustrating the main configuration of an automatic analyzer according to an embodiment of the present invention. An automatic analyzer 1 includes a measurement system 2 and a control analysis system 40. The measurement system 2 dispenses a sample, such as a specimen, and a reagent to a reaction vessel and performs optical measurement on liquid within the reaction vessel. The control analysis system 40 performs driving control on the measurement system 2 and performs an immunological analysis on a sample component based on the measurement result performed by the measurement system 2. These two systems cooperate to perform an immunological analysis on a plurality of sample components automatically and continuously. The following explanation is made assuming that the automatic analyzer 1 performs immunological measurement using a heterogeneous reaction.

As illustrated in FIG. 1, the measurement system 2 includes a specimen transferring unit 3, a carrier reagent table 5, a liquid reagent table 6, a reaction table 7, a specimen dispensing unit 8, a carrier reagent dispensing unit 9, a liquid reagent dispensing unit 10, a stirring unit 13, a photometry unit 14, and a cleaning device 20.

The specimen transferring unit 3 mounts thereon a plurality of racks 4, each of which holds specimen vessels 4a for accommodating specimens, and sequentially transfers the plurality of racks 4. The carrier reagent table 5 holds a plurality of carrier reagent vessels 5a arranged in a circumferential direction and has a driving unit for rotating it in a circumferential direction. The carrier reagent vessel 5a accommodates a carrier reagent that is used for an antigen-antibody reaction with a specimen. The liquid reagent table 6 holds liquid reagent vessels 6a that accommodate various types of liquid reagents. The liquid reagent table 6 has a driving unit for rotating it in a circumferential direction, which is different from the driving unit of the carrier reagent table 5. The reaction table 7 holds reaction vessels 7a, in which reactions between specimens and reagents are caused, and has a driving unit for rotating it in a circumferential direction similarly to the carrier reagent table 5.

The temperature of each table is kept constant. For example, the liquid reagent table 6 is set to a temperature lower than a room temperature to suppress the degradation and denaturation of a reagent. The reaction table 7 is set to a temperature equal to a human body temperature.

The specimen dispensing unit 8 dispenses specimens accommodated in the specimen vessels 4a on the specimen transferring unit 3 to the reaction vessels 7a held on the reaction table 7. The carrier reagent dispensing unit 9 dispenses carrier reagents accommodated in the carrier reagent vessels 5a on the carrier reagent table 5 to the reaction vessels 7a. The liquid reagent dispensing unit 10 dispenses liquid reagents accommodated in the liquid reagent vessels 6a on the liquid reagent table 6 to the reaction vessels 7a.

The specimen vessel 4a includes an information code recording medium (not shown) affixed thereto that records identification information for identifying a specimen accommodated therein by coding the identification information to an information code such as a bar-code or a two-dimensional code. Similarly, the carrier reagent vessel 5a and the liquid reagent vessel 6a each include an information code recording medium (not shown) affixed thereto that records identification information for identifying a reagent accommodated therein by coding the identification information to an information code. The measurement system 2 includes an information code reading unit CR1 that reads an information code affixed to the specimen vessel 4a, an information code reading unit CR2 that reads an information code affixed to the carrier reagent vessel 5a, and an information code reading unit CR3 that reads an information code affixed to the liquid reagent vessel 6a.

The specimen dispensing unit 8, the carrier reagent dispensing unit 9, and the liquid reagent dispensing unit 10 each include a canalicular probe that performs the suction and discharge of a specimen, an arm that moves the probe up and down in a vertical direction and rotates the probe in a horizontal direction, and a suction/discharge mechanism that uses a suction/discharge syringe or the like. In order to prevent contamination and carry-over, a disposable method is employed. A removable chip is attached to the leading end of the probe. The chip is exchanged for each dispensing operation. The specimen dispensing unit 8 includes, on an operation line thereof, a chip storing unit 8a for storing unused chips and a chip discarding unit 8b for discarding used chips.

A reaction vessel transferring unit 11 transfers the reaction vessel 7a in order to place the reaction vessel 7a on the reaction table 7 or to remove the reaction vessel 7a from the reaction table 7. The reaction vessel transferring unit 11 includes, on an operation line thereof, a reaction vessel storing unit 11a for storing unused reaction vessels 7a and a reaction vessel discarding unit 11b for discarding used reaction vessels 7a. The reaction vessel transferring unit 11 may have any configuration as far as it transfers liquid without spilling the liquid in the reaction vessel 7a.

The stirring unit 13 stirs liquid accommodated in the reaction vessel 7a. The photometry unit 14 includes a photomultiplier tube that measures weak light emitted by reaction liquid within the reaction vessel 7a. In case of measuring fluorescent light that is generated from reaction liquid, the photometry unit 14 may be provided with a light source for irradiating exciting light.

Figure 2:
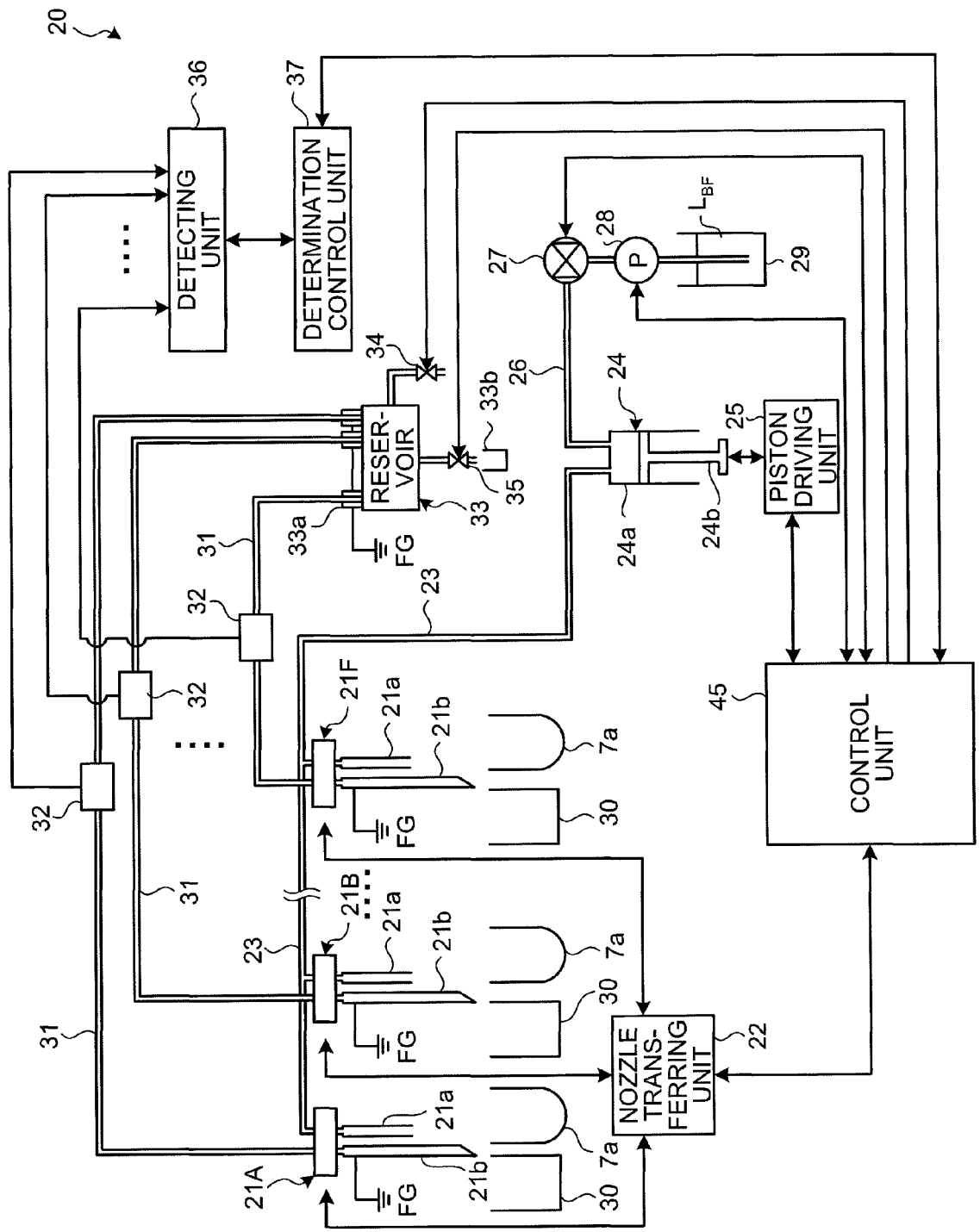
FIG. 2 is a schematic explanation diagram illustrating the schematic configuration of a cleaning device.

The cleaning device 20 performs B/F cleaning of a carrier reagent and cleaning of a suction nozzle 21b as illustrated in FIG. 2. The cleaning device 20 includes a plurality of B/F cleaning nozzle pairs 21A to 21F, each of which has as a pair a discharge nozzle 21a that discharges B/F cleaning liquid and the suction nozzle 21b that sucks liquid. The suction nozzle 21b is made of metal excellent in electrical conductivity, such as aluminum. The lower end of the suction nozzle 21b is positioned lower than the lower end of the discharge nozzle 21a. Each of the B/F cleaning nozzle pairs 21A to 21F is transferred to a nozzle cleaning tank 30 every time B/F cleaning after an immune reaction in the reaction vessel 7a is completed using a nozzle transferring unit 22. The nozzle transferring unit 22 collectively moves vertically and horizontally and rotates horizontally the B/F cleaning nozzle pairs 21A to 21F. Then, the suction nozzle 21b is cleaned by the B/F cleaning liquid discharged from the discharge nozzle 21a. A control unit 45 controls the vertical movement of the nozzle transferring unit 22 using a top point at a position raised in a vertical direction as an original point.

Because the nozzle transferring unit 22 collectively transfers the B/F cleaning nozzle pairs 21A to 21F, relative position relationships between the discharge nozzle 21a and the suction nozzle 21b of the nozzle pairs are not changed before and after the transfer. Incidentally, the nozzle transferring unit 22 is capable of transferring the nozzle pairs individually.

The discharge nozzles 21a are connected to a syringe 24 via a common pipe 23. The syringe 24 includes a cylinder 24a and a piston 24b. B/F cleaning liquid LBF is introduced into the pipe 23 and the cylinder 24a. In the syringe 24, the operation of the piston 24b is controlled by a piston driving unit 25 that is controlled by the control unit 45. The syringe 24 is connected to a cleaning liquid vessel 29 that accommodates the B/F cleaning liquid LBF via a pipe 26. An injection valve 27 that controls the flow of the B/F cleaning liquid LBF and a pump 28 that sucks the B/F cleaning liquid LBF from the cleaning liquid vessel 29 are provided in the pipe 26. When the B/F cleaning liquid LBF is to be introduced into the pipe 23 and the cylinder 24a, the injection valve 27 is opened, the B/F cleaning liquid LBF is filled up into the discharge nozzle 21a, the syringe 24, the pipes 23 and 26 using the pump 28, and then the injection valve 27 is closed to terminate the operation of the pump 28.

Each of the suction nozzles 21b of the B/F cleaning nozzle pairs 21A to 21F is connected to a reservoir 33 via an individual pipe 31. Each of the suction nozzles 21b is connected to a frame ground FG of the automatic analyzer 1. Each of the pipes 31 has the same diameter between the suction nozzle 21b and the reservoir 33 and provided with a detection electrode 32 at a mid point between the suction nozzle 21b and the reservoir 33. The detection electrode 32 is provided at the position such that an amount of the B/F cleaning liquid existing between the suction nozzle 21b and the detection electrode 32 is smaller than an amount of the B/F cleaning liquid within the cleaning tank 30. The distance between the suction nozzle 21b and the detection electrode 32 is set to be equal to or shorter than the distance between the detection electrode 32 and a reservoir electrode 33a.

The detection electrode 32 detects the change of electrostatic capacity caused by the B/F cleaning liquid flowing through the pipe 31 between the suction nozzle 21b and the detection electrode 32 or between the detection electrode 32 and the reservoir electrode 33a of the reservoir 33, and outputs an electrical signal corresponding to the change of electrostatic capacity to a detecting unit 36.

The reservoir 33 is connected to a vacuum pump, which causes negative pressure in the reservoir 33, via a pipe that has a suction valve 34. The reservoir 33 is provided with the reservoir electrodes 33a at locations to which the respective pipes 31 are connected. One end of the reservoir electrode 33a is connected to the B/F cleaning liquid flowing through the pipe 31 and the other end is connected to the frame ground FG of the automatic analyzer 1. The reaction liquid sucked from the reaction vessel 7a and the B/F cleaning liquid sucked from the nozzle cleaning tank 30 are discharged from the reservoir 33 to an external waste liquid tank 33b through a pipe that has an exhaust valve 35.

Figure 3:
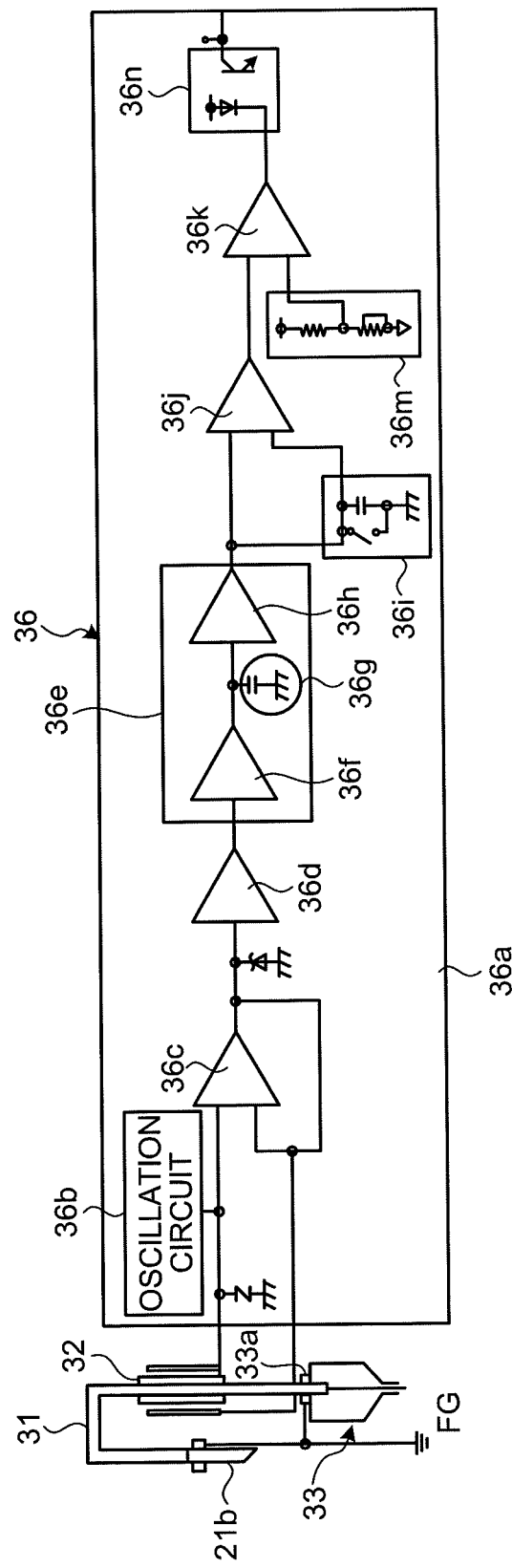
FIG. 3 is a block diagram illustrating a detecting unit of the cleaning device.

The detecting unit 36 detects the change of electrostatic capacity between the suction nozzle 21b and the reservoir electrode 33a as a binarized waveform that is a difference relative to a threshold voltage. The detecting unit 36 is provided on a detection board 36a for each of the B/F cleaning nozzle pairs 21A to 21F. As illustrated in FIG. 3, the detecting unit 36 includes an oscillation circuit 36b, an I-V converting unit 36c, a filter 36d, a DC converting unit 36e, a peak-hold circuit 36i, a differential amplifier 36j, and a comparator 36k.

The I-V converting unit 36c converts the change of electrostatic capacity output from the detection electrode 32 provided in the pipe 31 of the suction nozzle 21b into the change of an alternating voltage using an alternating current signal output from the oscillation circuit 36b. The filter 36d is a bandpass filter that passes only a signal near oscillating frequency oscillated by the oscillation circuit 36b and removes noises included in the change of alternating voltage converted by the I-V converting unit 36c. The DC converting unit 36e converts voltage variation of alternating current signal into voltage variation of direct current that has less ripples using a rectifying device 36f, a smoothing circuit 36g, and a long pass filter 36h.

The peak-hold circuit 36i is a circuit that detects whether the B/F cleaning liquid passes the detection electrode 32 with high precision using the change of electrostatic capacity relative to a reference of electrostatic capacity. The reference is an electrostatic capacity when the suction nozzle 21b does not suck the B/F cleaning liquid. The peak-hold circuit 36i holds a direct voltage before the electrostatic capacity is changed as a reference voltage. In order to use a stable electrostatic capacity as a reference, the peak-hold circuit 36i resets the previous reference voltage saved in the peak-hold circuit 36i of each of the detecting units 36 and holds the present new direct voltage as a reference voltage when the B/F cleaning liquid is discharged from one of the discharge nozzles 21a of the B/F cleaning nozzle pairs 21A to 21F in the nozzle cleaning tank 30. At that time, the control unit 45 that receives a signal output from the piston driving unit 25 inputs a peak-hold reset signal to the peak-hold circuit 36i.

The differential amplifier 36j outputs a voltage variation amount between the reference voltage held in the peak-hold circuit 36i and the voltage variation of the direct current converted by the DC converting unit 36e. The comparator 36k compares the voltage variation amount input from the differential amplifier 36j with a threshold voltage set in a binarization threshold circuit 36m and outputs a binarized waveform (see FIGS. 10 to 12, FIG. 14, and FIG. 15) that is a difference between the voltage variation amount and the threshold voltage to a determination control unit 37 via a photo coupler 36n. The binarized threshold value, i.e., the threshold voltage is set to an intermediate value between a voltage value when an electrostatic capacity caused by the B/F cleaning liquid flowing through the pipe 31 is largest and a voltage value when the electrostatic capacity is smallest.

Figure 4:
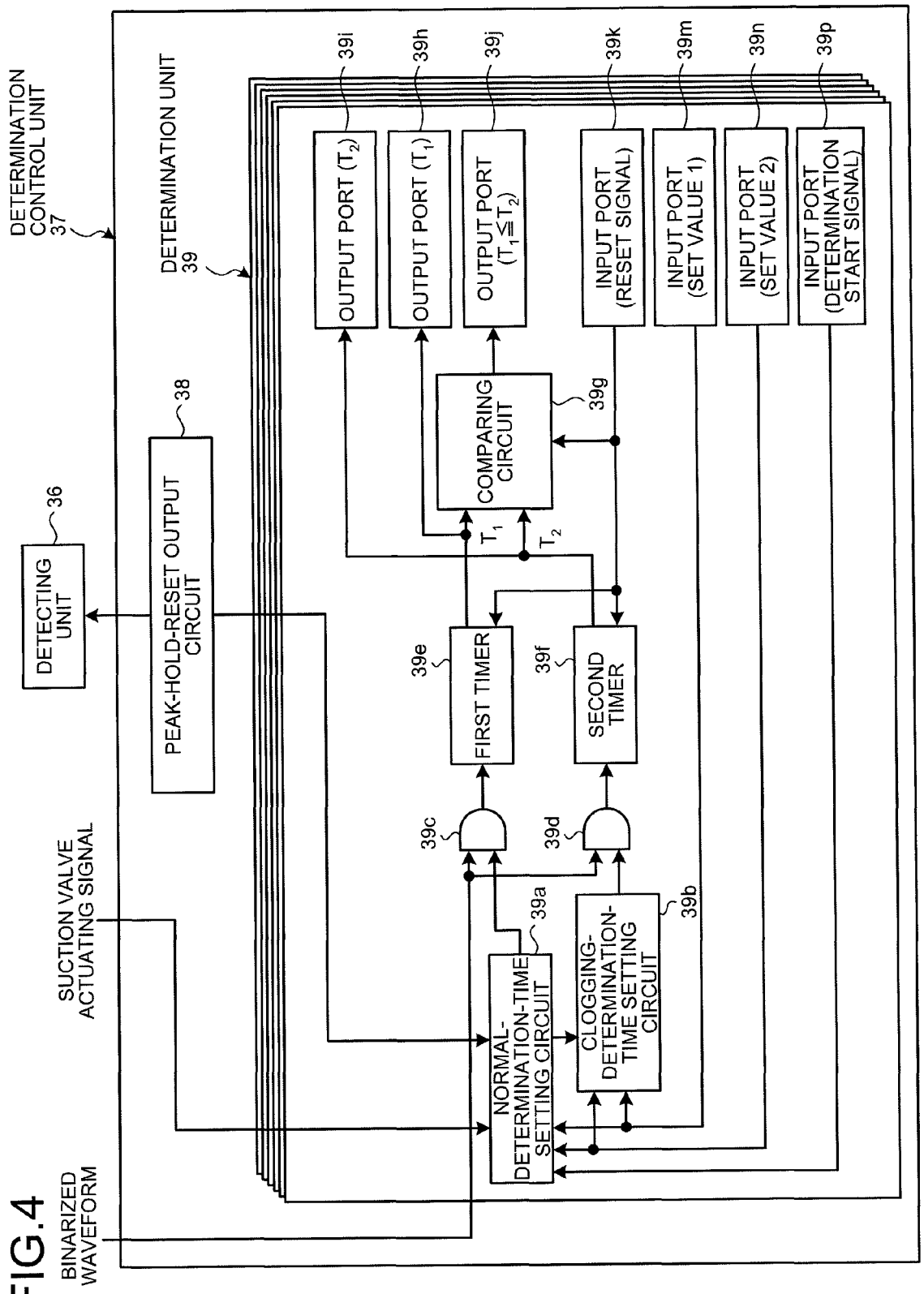
FIG. 4 is a block diagram illustrating a determination control unit of the cleaning device.

As illustrated in FIG. 4, the determination control unit 37 includes a peak-hold-reset output circuit 38 and determination units 39 that are respectively provided for the B/F cleaning nozzle pairs 21A to 21F and respectively determine whether the suction nozzles 21b are clogged.

The peak-hold-reset output circuit 38 outputs a peak-hold reset signal to the peak-hold circuit 36i of the detecting unit 36. Concerning the peak-hold reset signal, a timing at which cleaning liquid is discharged to the reaction vessel 7a is extracted from a driving signal for the syringe 24 and a driving signal for the B/F cleaning nozzle pairs 21A to 21F that are output from the piston driving unit 25 and the nozzle transferring unit 22 and are input to the peak-hold-reset output circuit 38 via the control unit 45. The peak-hold reset signal is pulse-shaped.

The determination unit 39 totalizes binarized waveforms input from the detecting unit 36 and determines whether the suction nozzle 21b is clogged. As illustrated in FIG. 4, the determination unit 39 includes a normal-determination-time setting circuit 39a, a clogging-determination-time setting circuit 39b, a first timer 39e, a second timer 39f, and a comparing circuit 39g.

The normal-determination-time setting circuit 39a sets the starting point and ending point of a normal determination time based on a determination start signal input from a storage unit 44 through an input port 39p and a set value 1 input through an input port 39m, and outputs the points to an AND circuit 39c. The ending point of the normal determination time is the starting point of a clogging determination time. The AND circuit 39c extracts ON components of a binarized waveform, which is input from the normal-determination-time setting circuit 39a, during the normal determination time and outputs the ON components to the first timer 39e.

The clogging-determination-time setting circuit 39b sets the ending point of the clogging determination time based on a set value 2 input from the storage unit 44 through an input port 39n, and outputs the point to an AND circuit 39d. The AND circuit 39d extracts ON components of a binarized waveform, which is input from the clogging-determination-time setting circuit 39b, during the clogging determination time and outputs the ON components to the second timer 39f.

The first timer 39e totalizes the ON components of the binarized waveform, which is input from the AND circuit 39c, during the normal determination time and outputs a totalizing time T1 to the comparing circuit 39g and an output port 39h. The second timer 39f totalizes the ON components of the clogging determination time having a binarized waveform input from the AND circuit 39d, and outputs a totalizing time T2 to the comparing circuit 39g and an output port 39i.

The comparing circuit 39g compares the totalizing time T1 and the totalizing time T2 input from the first timer 39e and the second timer 39f. The comparing circuit 39g then determines that the suction nozzle 21b is clogged when the totalizing time T2 is not less than the totalizing time T1 (T1≤T2) and outputs the determination to an output port 39j.

The totalizing time T1 output to the output port 39h, the totalizing time T2 output to the output port 39i, and the determination result of the effect that the suction nozzle 21b is clogged output to the output port 39j are output from the output ports to the storage unit 44. A reset signal read from the storage unit 44 by the control unit 45 is input to an input port 39k.

The detecting unit 36 and the determination control unit 37 are illustrated separately from the control unit 45 in FIG. 2. However, in order to simplify the configuration, the automatic analyzer 1 of the present invention utilizes the control unit 45 as the detecting unit 36 and the determination control unit 37 to be integrated with the control unit 45.

In the cleaning device 20 having the above-described configuration and function, operations of the nozzle transferring unit 22, the piston driving unit 25, the injection valve 27, the pump 28, the suction valve 34, and the exhaust valve 35 are controlled by the control unit 45 of the control analysis system 40.

In the measurement system 2 having the above-described configuration, a rotation angle of the reaction table 7 rotated by one rotation actuation is previously determined. All components are arranged so that dispensing of a specimen or various types of reagents can be performed simultaneously and variously together with this rotation. Thus, FIG. 1 is a diagram only schematically illustrating the components of the measurement system 2. In other words, a mutual positional relationship between the components of the measurement system 2 is a design matter to be determined in accordance with a condition such as a rotation mode of the wheel of the reaction table 7.

The control analysis system 40 includes an analysis computing unit 41, an input unit 42, an output unit 43, the storage unit 44, and the control unit 45.

The analysis computing unit 41 performs analysis calculation on the measurement result obtained in the measurement system 2. The input unit 42 inputs an actuation instruction signal of the automatic analyzer 1 and information required for the analysis of a specimen. The input unit 42 is realized by a keyboard, a mouse, a microphone, and the like. The output unit 43 outputs information including an analysis result, and is realized by a display (CRT, liquid crystal, plasma, organic EL, and the like), a printer, a speaker, and the like.

The storage unit 44 stores therein information including various types of parameters related to the automatic analyzer 1 or the cleaning device 20 in addition to the analysis result. The storage unit 44 includes a hard disk that magnetically stores various information and a memory that loads, when the automatic analyzer 1 and the cleaning device 20 perform various types of processes, programs related to the processes from the hard disk and electrically records the programs. During initialization, the control unit 45 reads the set values 1 and 2 for setting the normal determination time and the clogging determination time, the reset signal, and the determination start signal from the storage unit 44, and outputs these signals to the determination control unit 37. The set values 1 and 2 are set at the time of maintenance of the automatic analyzer 1 and are input to the storage unit 44.

The reset signal is a signal for resetting the totalizing time (T1) totalized by the first timer 39e of the determination unit 39, the totalizing time (T2) totalized by the second timer 39f, and the determination result (T1≤T2) performed in the comparing circuit 39g, and is input from the input port 39k (see FIG. 4) to the determination unit 39. The determination start signal is a signal for instructing the determination control unit 37 to start determination. The determination start signal is output from the control unit 45 to the determination unit 39 during a period from a time, at which the discharge of the B/F cleaning liquid from the discharge nozzle 21a to the reaction vessel 7a has started in response to the start of drive of the piston driving unit 25, to a time, at which the discharge nozzle 21a and the suction nozzle 21b are transferred to the nozzle cleaning tank 30 by the nozzle transferring unit 22 and the B/F cleaning liquid is discharged to the nozzle cleaning tank 30 to start the nozzle cleaning.

The storage unit 44 may further include an auxiliary storage device that can read information recorded in a recording medium such as a flexible disk, CD-ROM, DVD-ROM, a magnet-optical disk, a PC card, or an xD picture card.

The control unit 45 controls the automatic analyzer 1 and reads a program stored in the storage unit 44 from the memory to perform analysis calculation using the measurement result in the measurement system 2, the control of various types of actuations of the automatic analyzer 1, and the like.

When the control analysis system 40 having the above configuration receives a photometric result of weak light emitted by reaction liquid from the photometry unit 14, the analysis computing unit 41 computes an amount of luminescence of the reaction liquid within the reaction vessel 7a and uses a calibration curve obtained from a normal specimen and an analysis parameter included in the analysis information in addition to the computation result in order to quantitatively calculate the component of reaction liquid. The analysis result obtained in this way is output from the output unit 43 and is further stored in the storage unit 44.

The cleaning device 20 of the present invention having the above configuration performs vertical movements and horizontal movements of the plurality of B/F cleaning nozzle pairs 21A to 21F using the nozzle transferring unit 22 so as to perform the B/F cleaning of the reaction vessel 7a and internal/external cleaning of the suction nozzle 21b in the cleaning tank 30. An example of a time chart in which the B/F cleaning in the reaction vessel 7a and the cleaning of the suction nozzle 21b in the cleaning tank 30 are performed in one cleaning period is illustrated in FIG. 5.

Figure 5:
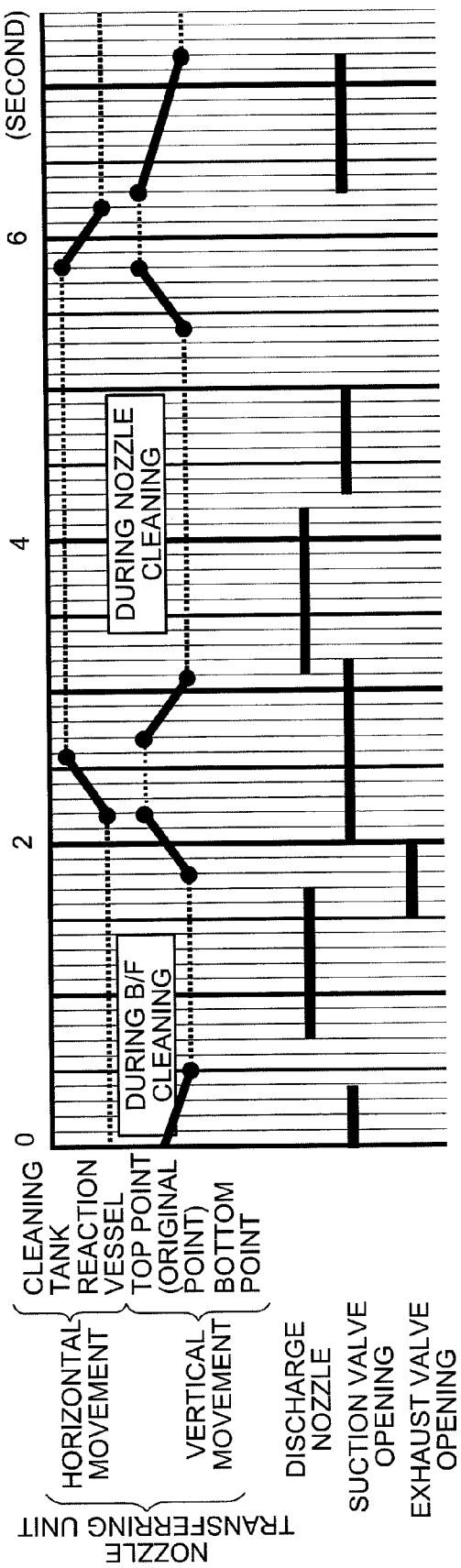
FIG. 5 is a diagram illustrating an example of a time chart, in which one cleaning period contains B/F cleaning in a reaction vessel and suction-nozzle cleaning in a cleaning tank.

FIG. 5 is a time chart regarding the movement of the nozzle transferring unit 22 that transfers the discharge nozzle 21a and the suction nozzle 21b of one of the B/F cleaning nozzle pairs, the discharge of the B/F cleaning liquid performed by the discharge nozzle 21a, the opening (nozzle cleaning with the sucking of the B/F cleaning liquid performed by the suction nozzle 21b) of the suction valve 34 that causes negative pressure in the reservoir 33, and the opening of the exhaust valve 35 that discharges liquid (reaction liquid and B/F cleaning liquid) within the reservoir 33. In FIG. 5, solid lines show a horizontal movement or a vertical movement of one of the B/F cleaning nozzle pairs performed by the nozzle transferring unit 22, the discharge of the B/F cleaning liquid from the discharge nozzle 21a, and the opening of the suction valve 34 and the opening of the exhaust valve 35. Dotted lines show that the nozzle transferring unit 22 does not move. In FIG. 5, parts that do not have marks for the opening of the suction valve 34 and the exhaust valve 35 indicate that the valves are closed.

As illustrated in FIG. 5, in the cleaning device 20, the nozzle transferring unit 22 moves the B/F cleaning nozzle pairs downward at the position of the reaction vessel 7a from 0 second to 0.5 second and then stops the pairs at a bottom point from 0.5 second to 1.8 second, and then moves the B/F cleaning nozzle pairs upward toward the top point from 1.8 second to 2.2 second and stops the pairs. During that time, the suction valve 34 is opened from 0 second to 0.4 second to causes negative pressure in the reservoir 33, and the reaction liquid within the reaction vessel 7a is sucked into the reservoir 33 by the suction nozzle 21b. The discharge nozzle 21a discharges the B/F cleaning liquid into the reaction vessel 7a from 0.7 second to 1.7 second to perform B/F cleaning on the inside of the reaction vessel 7a. The exhaust valve 35 is opened from 1.5 second to 2.0 second, the sucked reaction liquid is discharged from the reservoir 33, and the B/F cleaning of the reaction vessel 7a is completed. Because the suction valve 34 is opened from 2.0 second to 3.2 second and causes negative pressure in the reservoir 33, the suction nozzle 21b sucks part of the B/F cleaning liquid within the reaction vessel 7a while being moved upward by the nozzle transferring unit 22.

Subsequently, the nozzle transferring unit 22 horizontally moves the B/F cleaning nozzle pairs from 2.2 second to 2.6 second from the position of the reaction vessel 7a toward the position of the cleaning tank 30 while keeping the pairs at the top point between 2.2 second and 2.7 second. The pairs are kept at the position of the cleaning tank 30 up to 5.8 second. The nozzle transferring unit 22 then horizontally moves the B/F cleaning nozzle pairs from 5.8 second to 6.2 second from the position of the cleaning tank 30 toward the position of another reaction vessel 7a and then stops the pairs between 6.2 second and 7.5 second. The nozzle transferring unit 22 moves the B/F cleaning nozzle pairs downward from 2.7 second to 3.1 second and then stops the pairs at the bottom point at the position of the cleaning tank 30 between 3.1 second and 5.4 second, and then moves the B/F cleaning nozzle pairs upward from 5.4 second to 5.8 second and then stops the pairs at the top point. The nozzle transferring unit 22 stops the B/F cleaning nozzle pairs at the top point between 5.8 second and 6.3 second, and then moves the B/F cleaning nozzle pairs downward from 6.3 second to 7.2 second and stops the pairs at the bottom point up to 7.5 second.

During that time, the discharge nozzle 21a discharges the B/F cleaning liquid to the cleaning tank 30 from 3.1 second to 4.2 second. With this, the outside of the suction nozzle 21b is cleaned. Also, the B/F cleaning liquid just discharged from the discharge nozzle 21a is sucked by the suction nozzle 21b up to 3.2 second due to the attractive force of the reservoir 33 that is in negative pressure between 2.0 second and 3.2 second. The inside pressure of the reservoir 33 again becomes negative by opening the suction valve 34 from 4.3 second to 5.0 second, and the B/F cleaning liquid within the cleaning tank 30 is sucked to clean the suction nozzle 21b. Then, the suction valve 34 is opened from 6.3 second to 7.2 second to cause negative pressure in the reservoir 33 and sucks reaction liquid within another reaction vessel 7a, toward which the move was made between 5.8 second and 6.2 second.

FIG. 5 illustrates a basic cleaning period of the cleaning device 20. The B/F cleaning of the reaction vessel 7a and the internal/external cleaning of the suction nozzle 21b in the cleaning tank 30 can be performed by changing times or combining a plurality of the cleaning period as needed.

Figure 6:
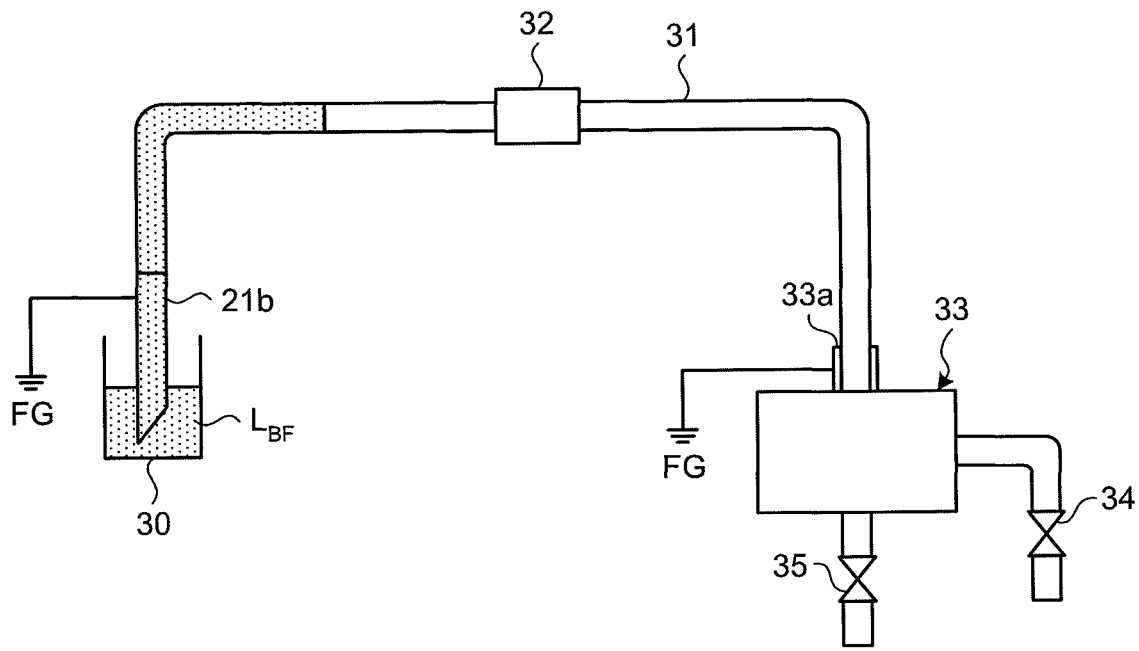
FIG. 6 is a schematic diagram illustrating the arrangement of a cleaning tank, a suction nozzle, a pipe, a detection electrode, and a reservoir and illustrating a state where B/F cleaning liquid is sucked between the suction nozzle and the reservoir.
Figure 7:
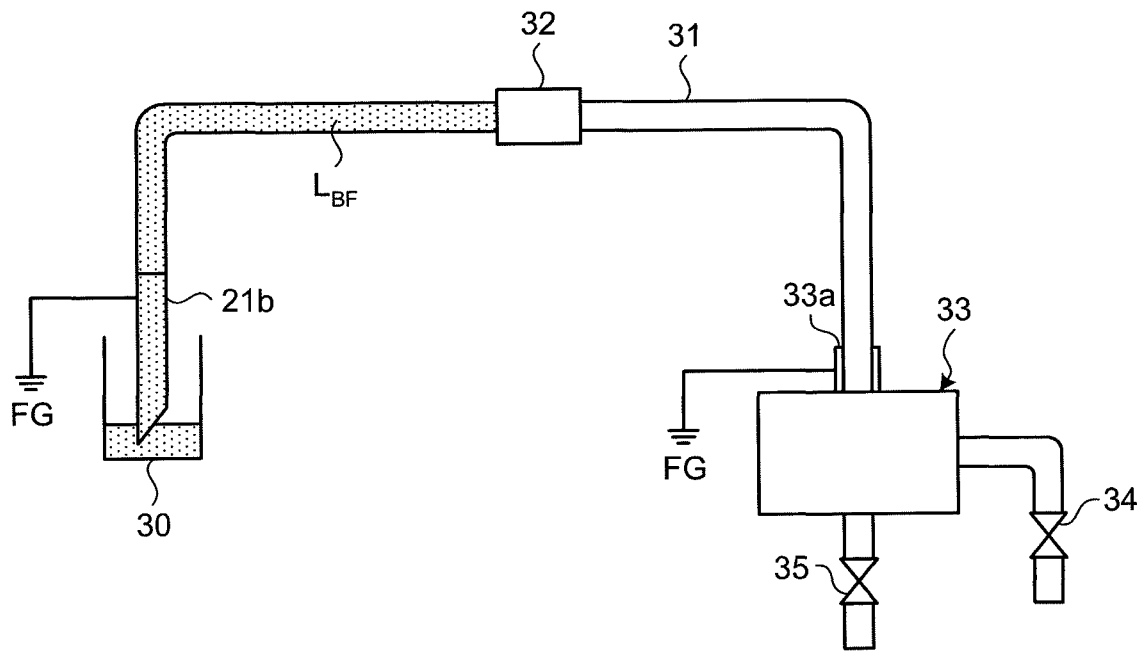
FIG. 7 is a diagram illustrating a state where the B/F cleaning liquid is further sucked from a position illustrated in FIG. 6, the leading end of the B/F cleaning liquid comes in contact with the detection electrode, and the suction nozzle and the detection electrode are connected to each other.

The nozzle transferring unit 22 moves the plurality of B/F cleaning nozzle pairs 21A to 21F to the cleaning tank 30, and the suction nozzle 21b sucks the B/F cleaning liquid, which has discharged by the discharge nozzle 21a to the cleaning tank 30, from the cleaning tank 30. Then, the B/F cleaning liquid within the cleaning tank 30 sucked by the suction nozzle 21b is discharged to the reservoir 33 through the pipe 31. In this way, the suction nozzle 21b is cleaned by the sucked B/F cleaning liquid. When the suction nozzle 21b sucks the B/F cleaning liquid from the cleaning tank 30, the B/F cleaning liquid LBF within the cleaning tank 30 is sucked into the pipe 31 as illustrated in FIG. 6. As illustrated in FIG. 7, when the leading end of the B/F cleaning liquid LBF within the pipe 31 comes in contact with the detection electrode 32, the electrostatic capacity is largely changed due to the B/F cleaning liquid LBF between the suction nozzle 21b and the detection electrode 32.

Figure 8:
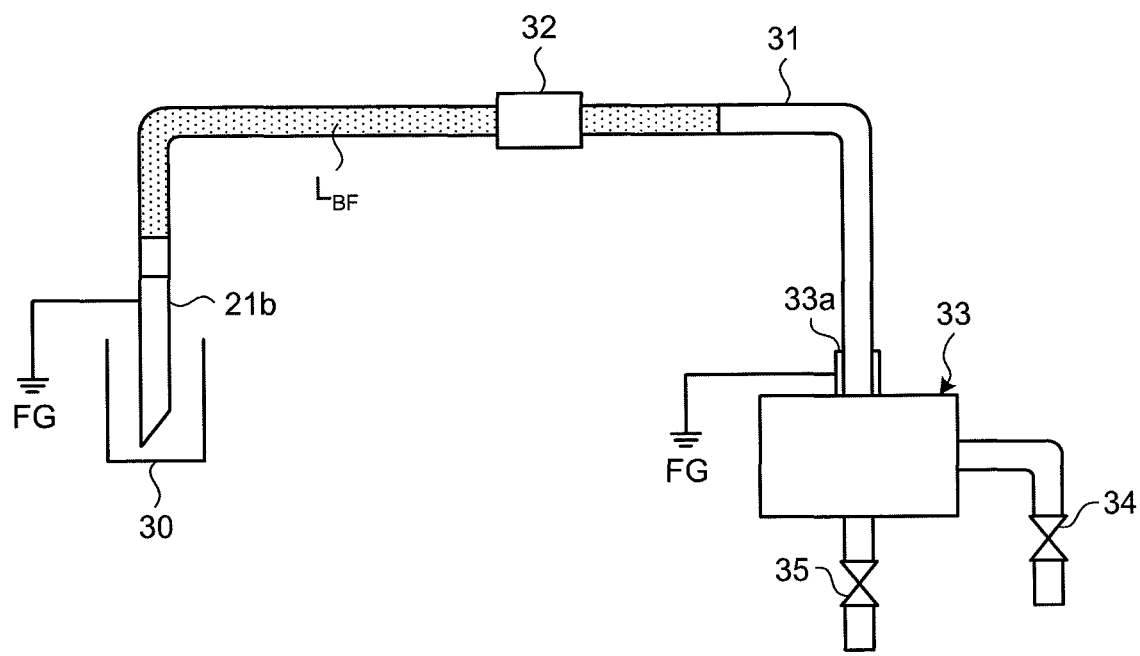
FIG. 8 is a diagram illustrating a state where the sucked B/F cleaning liquid is further sucked from a position illustrated in FIG. 7 and the leading end of the B/F cleaning liquid moves to a position between the detection electrode and the reservoir.
Figure 9:
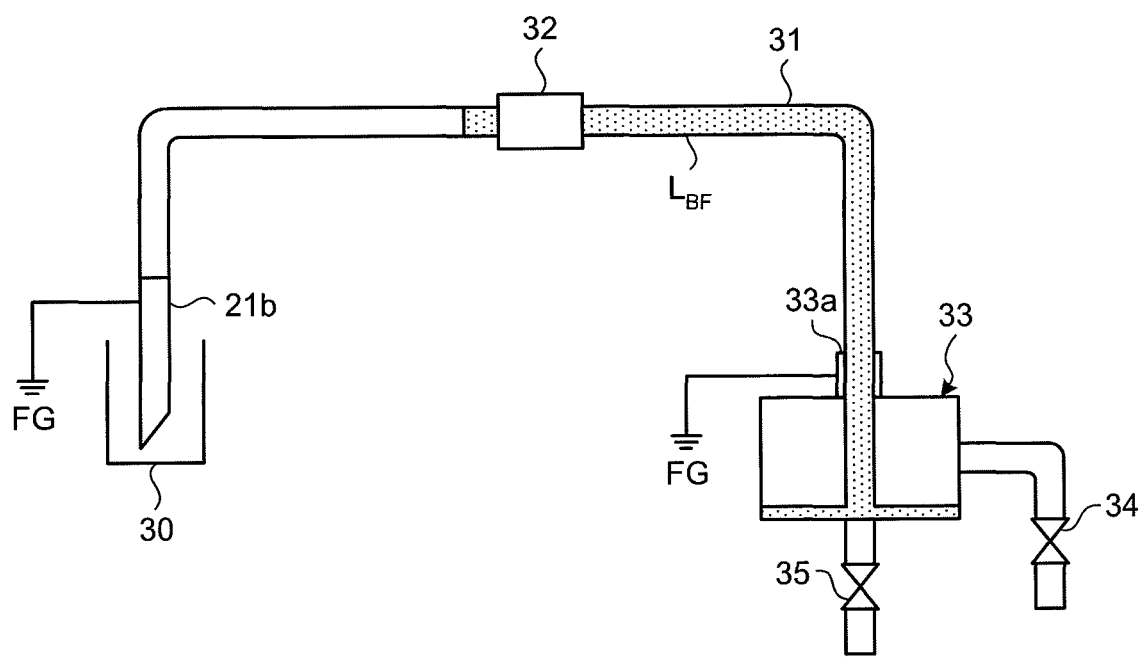
FIG. 9 is a diagram illustrating a state where the sucked B/F cleaning liquid is further sucked from a position illustrated in FIG. 8, the leading end of the B/F cleaning liquid comes in contact with the electrode of the reservoir, and the detection electrode and the electrode of the reservoir are connected to each other.

The suction nozzle 21b further sucks the B/F cleaning liquid LBF within the cleaning tank 30, and the electrostatic capacity becomes small when the leading end of the B/F cleaning liquid LBF within the pipe 31 has passed the detection electrode 32 and the rear end of the B/F cleaning liquid LBF has also passed the suction nozzle 21b as illustrated in FIG. 8. As illustrated in FIG. 9, when the leading end of the B/F cleaning liquid LBF within the pipe 31 arrives at the reservoir 33 and the rear end side of the B/F cleaning liquid LBF touches the detection electrode 32, an electrostatic capacity is largely changed again due to the B/F cleaning liquid LBF between the detection electrode 32 and the reservoir electrode 33a.

Figure 10:
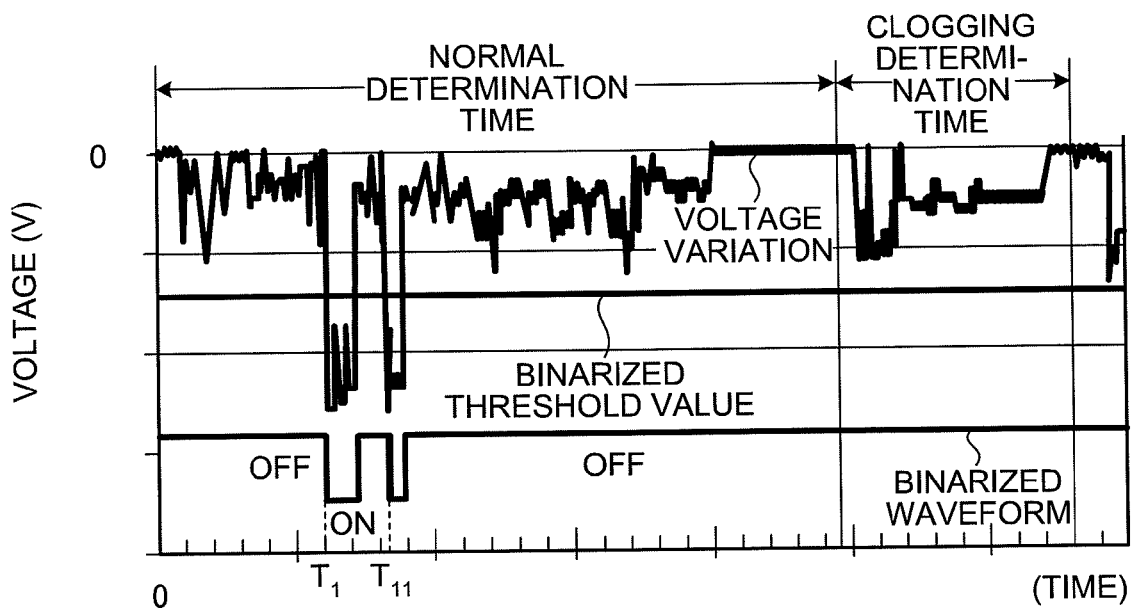
FIG. 10 is a diagram illustrating examples of a voltage variation, a threshold voltage, and a binarized waveform detected by the detecting unit on the basis of the change of electrostatic capacity caused by cleaning liquid flowing between the suction nozzle and the reservoir when the suction nozzle is not clogged.
Figure 11:
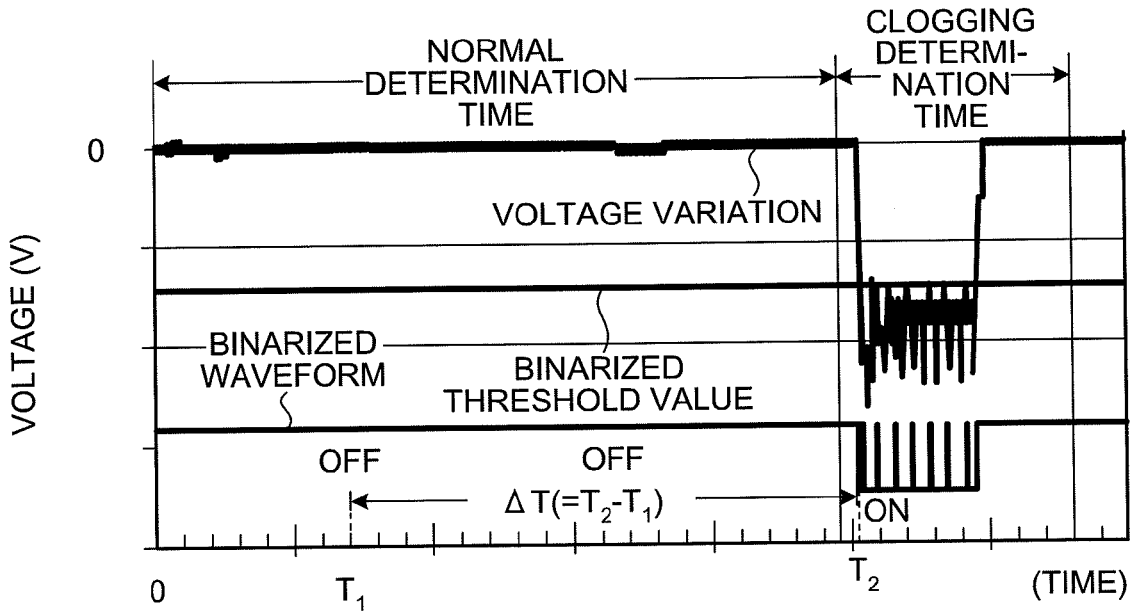
FIG. 11 is a diagram illustrating examples of a voltage variation, a threshold voltage, and a binarized waveform detected by the detecting unit on the basis of the change of electrostatic capacity caused by cleaning liquid flowing between the suction nozzle and the reservoir when the suction nozzle is partially clogged.
Figure 12:
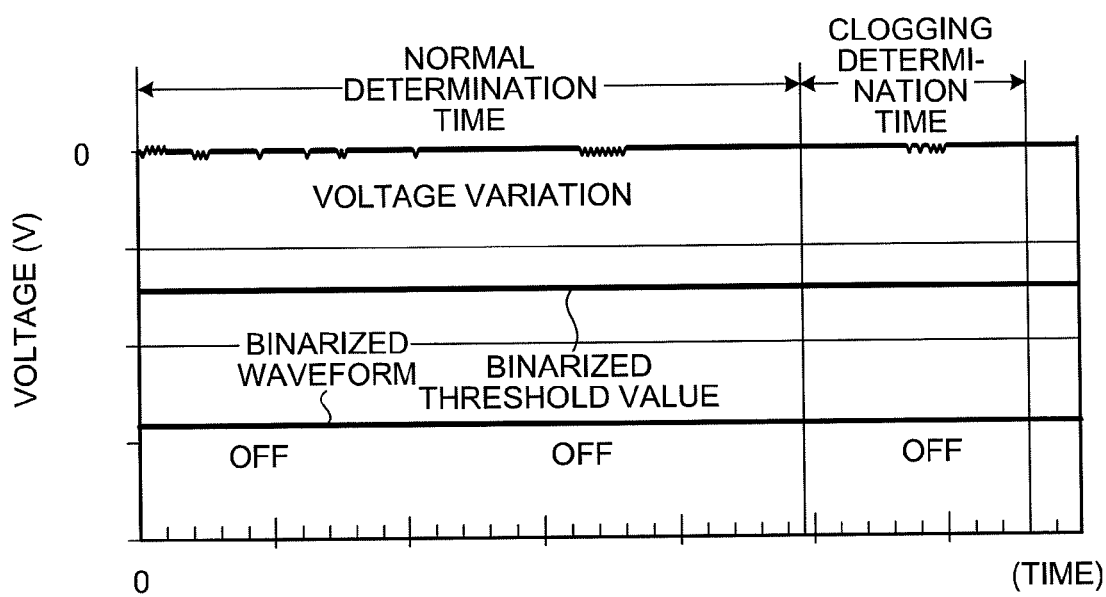
FIG. 12 is a diagram illustrating examples of a voltage variation, a threshold voltage, and a binarized waveform detected by the detecting unit on the basis of the change of electrostatic capacity caused by cleaning liquid flowing between the suction nozzle and the reservoir when the suction nozzle is perfectly clogged.

In the cleaning device 20, the detecting unit 36 detects the change of electrostatic capacity caused by the B/F cleaning liquid flowing through the pipe 31 as a binarized waveform that is a difference relative to a threshold voltage. FIG. 10 illustrates examples of a voltage variation, a threshold voltage, and a binarized waveform output from the differential amplifier 36j of the detecting unit 36 based on the change of electrostatic capacity when the suction nozzle 21b is not clogged with foreign materials. The normal determination time and the clogging determination time are also depicted. In FIG. 10, the binarized waveform has ON states at two points. The first ON state is detected when the leading end of the B/F cleaning liquid LBF within the pipe 31 passes the detection electrode 32 as illustrated in FIG. 7. The second ON state is detected when the leading end of the B/F cleaning liquid LBF within the pipe 31 arrives at the reservoir 33 and the rear end side of the B/F cleaning liquid LBF touches the detection electrode 32 as illustrated in FIG. 9. The time for which the binarized waveform has the ON state in the normal determination time illustrated in FIG. 10 is totalized by the first timer 39e of the determination unit 39 and is referred to as the totalizing time T1. In FIG. 10, the normal determination time starts at zero second and its horizontal axis shows a time scale. This is similar in FIGS. 11 and 12. FIGS. 10 to 12 are diagrams when the pipe 31 is not clogged.

When the suction nozzle 21b is partially clogged, the flow of the B/F cleaning liquid within the pipe 31 becomes slow. FIG. 11 illustrates examples of a voltage variation, a threshold voltage, and a binarized waveform output from the differential amplifier 36j of the detecting unit 36 in the normal determination time and the clogging determination time is. As illustrated in FIG. 11, because the flow of the B/F cleaning liquid within the pipe 31 is slow, the binarized waveform becomes an ON state in the clogging determination time after the termination of the normal determination time. Therefore, the time difference ($\Delta T$) is caused between the ON times of the binarized waveform illustrated in FIG. 11 and the binarized waveform illustrated in FIG. 10. The time for the binarized waveform becomes an ON state in the clogging determination time is totalized by the second timer 39f of the determination unit 39 as the totalizing time T2. When the suction nozzle 21b is perfectly clogged, because the suction nozzle 21b cannot suck the B/F cleaning liquid, the B/F cleaning liquid does not flow through the pipe 31. FIG. 12 illustrates examples of the voltage variation, the threshold voltage, and the binarized waveform output from the differential amplifier 36j of the detecting unit 36 in the normal determination time and the clogging determination time.

In the method for detecting suction nozzle clogging according to the present invention, the change of electrostatic capacity caused by the B/F cleaning liquid flowing through the pipe 31 is detected as a binarized waveform, and the presence or absence of the clogging of the suction nozzle 21b is determined based on the totalizing times T1 and T2 of the binarized waveform in the normal determination time and the clogging determination time.

Figure 13:
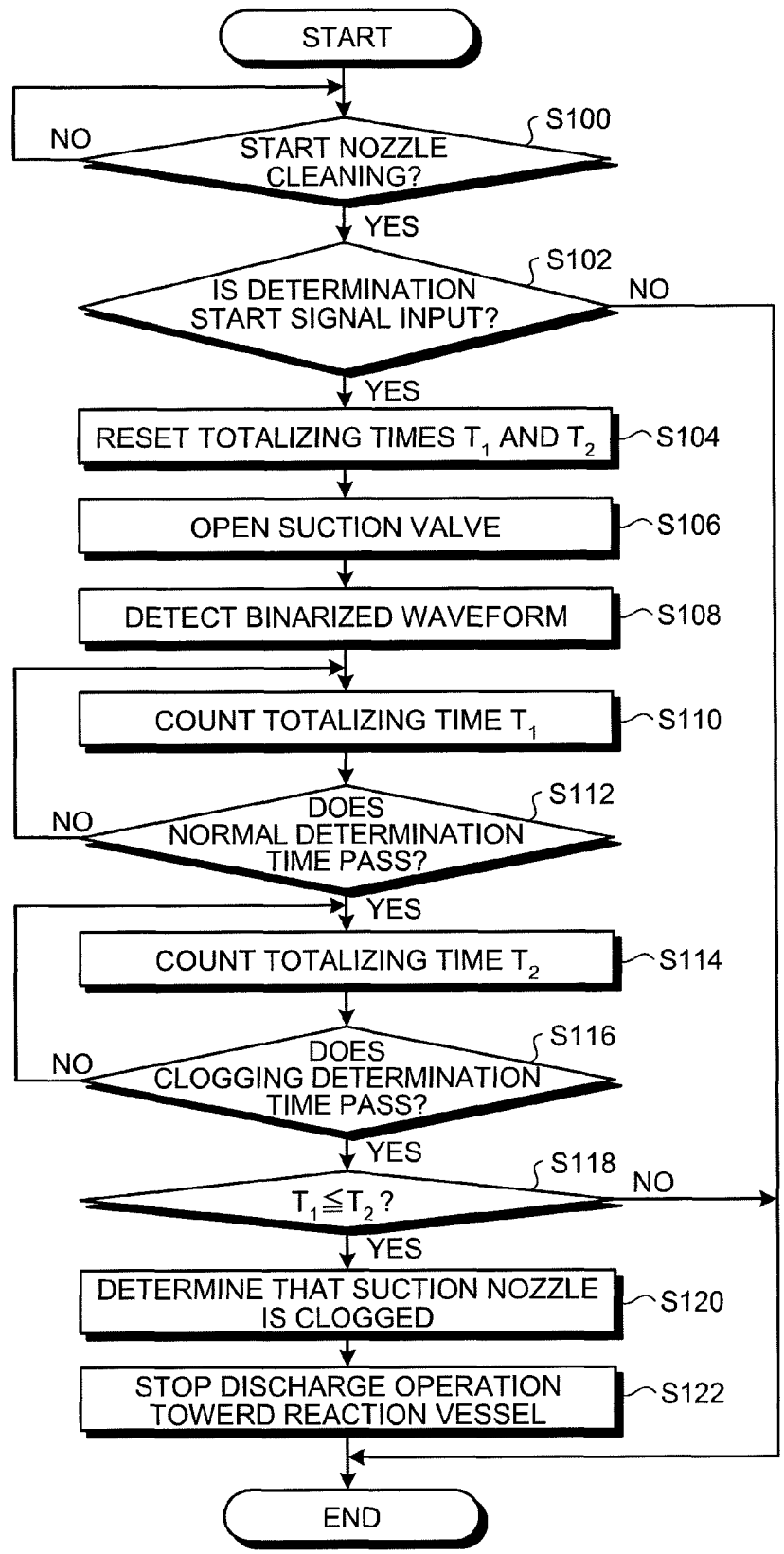
FIG. 13 is a flowchart explaining a method for detecting suction nozzle clogging that is performed in the cleaning device.

Hereinafter, the method for detecting suction nozzle clogging performed in the cleaning device 20 will be described with reference to the flowchart illustrated in FIG. 13.

First, when the electric source of the automatic analyzer 1 is turned on and the control unit 45 is initialized, the cleaning device 20 determines whether nozzle cleaning in the cleaning tank 30 is started (Step S100). This determination is made using a signal that is input from the piston driving unit 25, which causes the discharge nozzle 21a to discharge the B/F cleaning liquid, to the control unit 45. As a determination result, when the piston driving unit 25 does not operate and the B/F cleaning liquid is not discharged from the discharge nozzle 21a (Step S100: No), the determination of Step S100 is repeated.

When the piston driving unit 25 operates and the B/F cleaning liquid is discharged from the discharge nozzle 21a into the cleaning tank 30 (Step S100: Yes), the cleaning device 20 determines whether a determination start signal is input to the determination unit 39 of the determination control unit 37 (Step S102). This determination is made depending on whether the control unit 45 outputs the determination start signal that is read from the storage unit 44 to the determination unit 39. When the determination start signal is not input to the determination unit 39 (Step S102: No), the cleaning device 20 terminates the clogging detection of the suction nozzle 21b.

In contrast, when the determination start signal is input to the determination unit 39 (Step S102: Yes), the cleaning device 20 resets the totalizing times T1 and T2 (Step S104). The reset of the totalizing times T1 and T2 is performed by outputting the reset signal read from the storage unit 44 to the determination control unit 37 by the control unit 45.

Subsequently, the cleaning device 20 opens the suction valve 34 (Step S106). The opening of the suction valve 34 is performed by outputting an opening signal to the suction valve 34 by the control unit 45. In this way, negative pressure is caused in the reservoir 33, the B/F cleaning liquid within the cleaning tank 30 is sucked by the suction nozzle 21b, and the suction nozzle 21b is cleaned.

Subsequently, the cleaning device 20 detects the change of electrostatic capacity caused by the B/F cleaning liquid flowing through the pipe 31 as a binarized waveform (Step S108). The detection of the binarized waveform is executed by the detecting unit 36. After that, the cleaning device 20 counts the totalizing time T1 of the detected binarized waveform in the normal determination time (Step S110). The count of the totalizing time T1 is executed by the determination unit 39 to which the binarized waveform is input.

Then, the cleaning device 20 determines whether the normal determination time has passed (Step S112). This determination is made by the determination unit 39. When the normal determination time has not passed (Step S112: No), the cleaning device 20 returns the process control to Step S110 and repeats the count of the totalizing time T1. When the normal determination time has passed (Step S112: Yes), the cleaning device 20 counts the totalizing time T2 of the detected binarized waveform in the clogging determination time (Step S114). The count of the totalizing time T2 is executed by the determination unit 39 to which the binarized waveform is input.

Next, the cleaning device 20 determines whether the clogging determination time has passed (Step S116). This determination is made by the determination unit 39. When the clogging determination time has not passed (Step S116: No), the cleaning device 20 returns the process control to Step S114 and repeats the count of the totalizing time T2.

When the clogging determination time has passed (Step S116: Yes), the cleaning device 20 determines whether the totalizing time T2 is not less than the totalizing time T1 (Step S118). This determination is executed by the comparing circuit 39g of the determination unit 39. As a determination result, when the totalizing time T2 is less than the totalizing time T1, the B/F cleaning liquid flows through the pipe 31 within the normal determination time and the suction nozzle 21b is not clogged. Therefore, the cleaning device 20 terminates the clogging detection of the suction nozzle 21b.

In contrast, when the totalizing time T2 is not less than the totalizing time T1, the B/F cleaning liquid flows through the pipe 31 in the clogging determination time that is after the normal determination time. Thus, the cleaning device 20 determines that the suction nozzle 21b is clogged (Step S120). Therefore, the cleaning device 20 stops discharging the B/F cleaning liquid to the reaction vessel 7a (Step S122), and terminates the clogging detection of the suction nozzle 21b. The cleaning device 20 then causes the output unit 43 of the automatic analyzer 1 to display a warning such as the effect that the suction nozzle 21b is clogged or the requirement of maintenance.

When the cleaning operation of the suction nozzle 21b in the cleaning tank 30 is terminated, the nozzle transferring unit 22 of the cleaning device 20 returns the plurality of B/F cleaning nozzle pairs 21A to 21F to the position of the reaction vessel 7a of the reaction table 7 to start sucking the reaction liquid within the reaction vessel 7a. If the B/F cleaning liquid is discharged to the reaction vessel 7a when the suction nozzle 21b is clogged, the suction nozzle 21b cannot suck the reaction liquid within the reaction vessel 7a and thus the B/F cleaning liquid overflows from the reaction vessel 7a. Therefore, the cleaning device 20 stops discharging the B/F cleaning liquid to the reaction vessel 7a.

As described, the cleaning device 20 detects the change of electrostatic capacity between the suction nozzle 21b and the reservoir electrode 33a as a binarized waveform that is the difference relative to a threshold voltage, and determines whether the suction nozzle 21b is clogged based on the totalizing times T1 and T2 of the binarized waveform in the normal determination time and the clogging determination time. The reaction liquid sucked by the suction nozzle 21b during B/F cleaning has a large fluctuation range of an electrostatic capacity, whereas the B/F cleaning liquid is stable because of a small fluctuation range of an electrostatic capacity. Thus, it is preferable to use the B/F cleaning liquid in terms of the detection precision of electrostatic capacity or the accuracy of detection.

The cleaning device 20 detects whether the suction nozzle 21b is clogged based on the change of electrostatic capacity caused by the B/F cleaning liquid flowing through the pipe 31 between the suction nozzle 21b and the reservoir electrode 33a of the reservoir 33. The cleaning device 20 may alternatively detect whether the suction nozzle 21b is clogged based on the change of electrostatic capacity caused by the B/F cleaning liquid flowing through at least one of the pipe 31 between the suction nozzle 21b and the detection electrode 32 and the pipe 31 between the detection electrode 32 and the reservoir electrode 33a of the reservoir 33.

Figure 14:
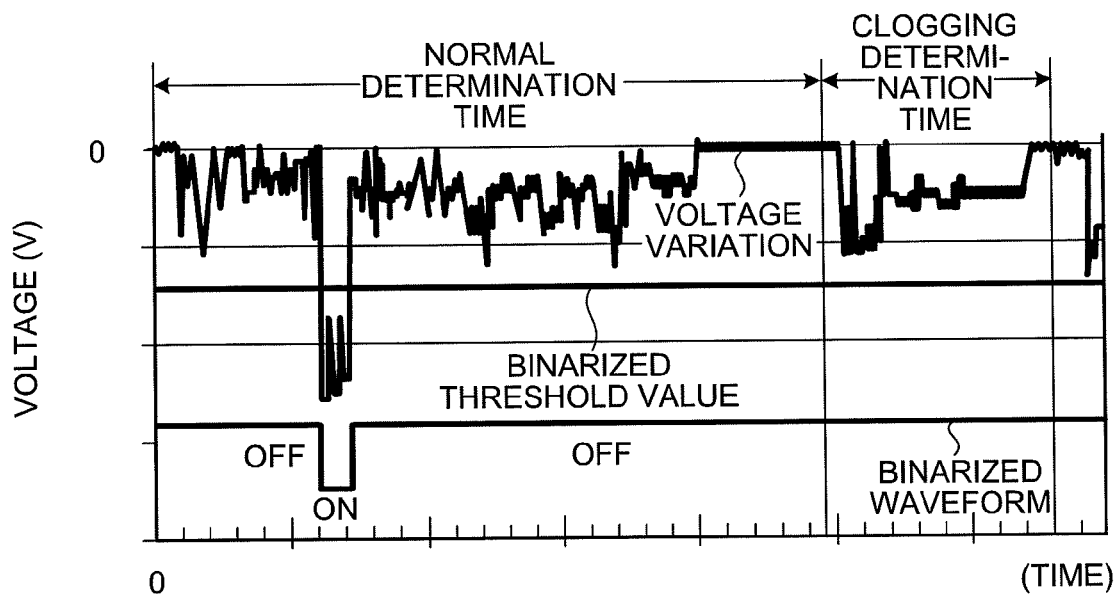
FIG. 14 is a diagram illustrating examples of a voltage variation, a threshold voltage, and a binarized waveform detected by the detecting unit on the basis of the change of electrostatic capacity caused by cleaning liquid flowing between the suction nozzle and the detection electrode when the suction nozzle is not clogged.

FIG. 14 illustrates examples of the voltage variation, the threshold voltage, and the binarized waveform output from the differential amplifier 36j of the detecting unit 36 based on the change of electrostatic capacity caused by the B/F cleaning liquid flowing through the pipe 31 between the suction nozzle 21b and the detection electrode 32 when the suction nozzle 21b is not clogged with foreign materials. FIG. 14 also indicates the normal determination time and the clogging determination time.

Figure 15:
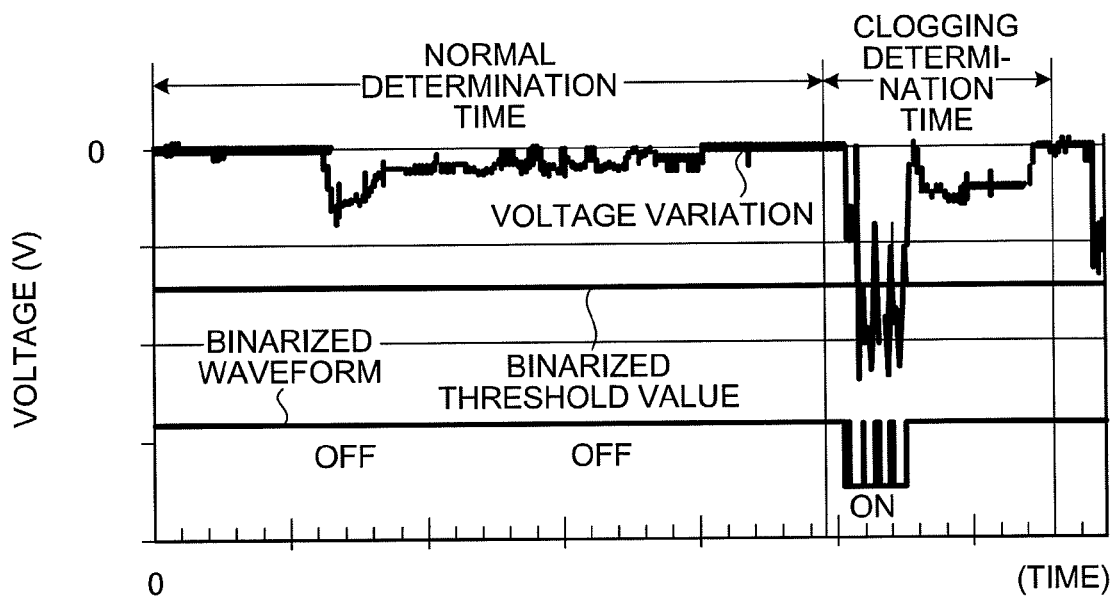
FIG. 15 is a diagram illustrating examples of a voltage variation, a threshold voltage, and a binarized waveform detected by the detecting unit on the basis of the change of electrostatic capacity in the same interval as that of FIG. 14 when the suction nozzle is partially clogged.

In contrast, FIG. 15 illustrates examples of the voltage variation, the threshold voltage, and the binarized waveform output from the differential amplifier 36j of the detecting unit 36 in the normal determination time and the clogging determination time when the suction nozzle 21b is partially clogged. When the suction nozzle 21b is perfectly clogged, the voltage variation, the threshold voltage, and the binarized waveform output from the differential amplifier 36j of the detecting unit 36 in the normal determination time and the clogging determination time are as illustrated FIG. 12.

The cleaning device 20 can determine whether the suction nozzle 21b is clogged by comparing the totalizing time T1 of the binarized waveform in the normal determination time with the totalizing time T2 of the binarized waveform in the clogging determination time that are calculated based on the change of electrostatic capacity between the suction nozzle 21b and the detection electrode 32. Similarly, the cleaning device 20 can detect whether the suction nozzle 21b is clogged based on the change of electrostatic capacity between the detection electrode 32 and the reservoir electrode 33a of the reservoir 33.

It is preferable that the cleaning device 20 detects whether the suction nozzle 21b is clogged based on the change of electrostatic capacity between the suction nozzle 21b and the reservoir electrode 33a of the reservoir 33 because the flow of the B/F cleaning liquid can be checked over the entire length of the pipe 31. However, it is advantageous that the cleaning device 20 detects whether the suction nozzle 21b is clogged based on the change of electrostatic capacity between the suction nozzle 21b and the detection electrode 32 because the clogging of the suction nozzle 21b can be quickly detected.

The cleaning device 20 can detect whether the suction nozzle 21b is clogged, using the time at which the binarized waveform becomes an ON state in the normal determination time illustrated in FIG. 10 as a standard and measuring the delay of the binarized waveform that is the time difference (ΔT) illustrated in FIG. 11 between the time and the time at which the binarized waveform becomes an ON state in the clogging determination time by the first timer 39e and the second timer 39f. In this case, the occurrence of temporal clogging of the suction nozzle 21b and the pipe 31 can be known using the length of the measured time difference (ΔT). If a relationship between the time at which the binarized waveform becomes an ON state in the determination time and the temporal clogging state of the suction nozzle 21b and the pipe 31 is previously checked and is recorded in the storage unit 44, the automatic analyzer 1 can automatically and previously notice the requirement of maintenance related to the B/F cleaning nozzle pairs 21A to 21F and the pipe 31 using the control unit 45.

In the cleaning period illustrated in FIG. 5, the transfer time and stop time of the B/F cleaning nozzle pairs performed by the nozzle transferring unit 22, the discharge time of the B/F cleaning liquid performed by the discharge nozzle 21a, and the opening time of the suction valve 34 and the opening time of the exhaust valve 35 can be appropriately changed in accordance with the B/F cleaning situation in the reaction vessel 7a and the cleaning situation of the suction nozzle 21b in the cleaning tank 30.

In the embodiment, only the normal determination time and clogging determination time are set. However, a gray zone time may be provided between the normal determination time and the clogging determination time so as to previously notice the maintenance of the B/F cleaning nozzle pairs 21A to 21F and the pipe 31.

In the above embodiment, the cleaning device, the method for detecting suction nozzle clogging, and the automatic analyzer that are used for an immunological test are described. However, the present invention can be used in the cleaning device, the method for detecting suction nozzle clogging, and the automatic analyzer that are used for a biochemical test or a gene test.

The configuration of the detecting unit 36 is not limited to that illustrated in FIG. 3 as far as it can detect the change of electrostatic capacity between the suction nozzle 21b and the reservoir electrode 33a as a binarized waveform that is the difference relative to a threshold voltage. Furthermore, the configuration of the determination control unit 37 is not limited to that illustrated in FIG. 4 as far as it includes the peak-hold-reset output circuit 38 that outputs a peak-hold reset signal to the peak-hold circuit 36i of the detecting unit 36 and the determination unit 39 that determines whether each of the suction nozzles 21b is clogged based on the binarized waveform input from the detecting unit 36.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A clog detection device for an analyzer comprising:
a suction nozzle, having a nozzle electrode associated therewith, that is configured for sucking liquid in a vessel;
a pipe connecting the suction nozzle to a discard vessel;
a first electrode coupled to the pipe;
a second electrode coupled to the pipe and disposed in between the nozzle electrode and the first electrode;
a detecting unit coupled to the suction nozzle, the first electrode, and the second electrode, wherein the detecting unit is programmed to (i) detect an output signal between first electrode and the second electrode, between the suction nozzle and the second electrode, or between the suction nozzle and the first electrode; (ii) compare the output signal to a threshold value; and (iii) output the difference between the output signal and the threshold value over time to a determination unit coupled to the detecting unit; and
the determination unit, wherein the determination unit is programmed to (i) set a preset normal determination time and a preset clogging determination time; and (ii) determine that the suction nozzle is clogged when a totalizing time, for which the output signal exceeds the threshold value during the preset clogging determination time, is longer than a totalizing time, for which the output signal exceeds the threshold value during the preset normal determination time.

2. The clog detection device of claim 1, wherein the suction nozzle is made of electroconductive material and wherein the nozzle electrode is integral therewith.

3. The clog detection device of claim 1, wherein the detecting unit is programmed to set the threshold value as a voltage value.

4. The clog detection device of claim 1, wherein the detecting unit is programmed to output the difference between the output signal and the threshold value over time in a waveform.

5. The clog detection device of claim 1, wherein the determination unit is programmed to determine that the nozzle is clogged when the totalizing time, for which the output signal exceeds the threshold value during the preset clogging determination time, equals the totalizing time, for which the signal value exceeds the threshold value during the preset normal determination time.

6. The clog detection device of claim 1, further comprising a discharge nozzle coupled to a cleaning liquid vessel storing cleaning liquid via a pump that discharges a cleaning liquid.

7. The clog detection device of claim 1, further comprising a discard vessel that is connected to the pipe to discard the liquid.

8. The clog detection device of claim 7, wherein the first electrode is coupled to the discard vessel via the pipe.

9. The clog detection device of claim 6, wherein the analyzer further comprises a control unit coupled to the determination unit and the pump, wherein the control unit is programmed to stop the discharge nozzle from discharging cleaning liquid when the determination unit determines that the suction nozzle is clogged.

10. The clog detection device of claim 1, further comprising a storage unit, wherein the storage unit stores information including the normal determination time and the clogging determination time.

11. The clog detection device of claim 1, further comprising a vacuum pump, wherein the suction nozzle is coupled to the vacuum pump.

12. The clog detection device of claim 1, wherein the detecting unit is programmed to detect that the output signal varies according to the flow of the liquid in the pipe.

13. An automatic analyzer comprising
a vessel,
a stirring unit configured to stir a specimen and a reagent in the vessel to cause a reaction,
a photometry unit configured for measuring an optical characteristic of reaction liquid in the vessel,
a control analysis system configured to analyze the reaction liquid in the vessel, and
the clog detection device of claim 1, wherein the suction nozzle is configured for sucking liquid from the vessel.

14. The automatic analyzer of claim 13, wherein the stirring unit is configured to stir reagent comprising a solid phase coupled to an antibody.

15. The automatic analyzer of claim 14, wherein the stirring unit is configured to stir a specimen component that binds the antibody in the reaction vessel.

16. The automatic analyzer of claim 13, wherein the stirring unit is configured to stir reagent comprising a solid phase coupled to an antigen that binds an antibody in the specimen.

17. An analyzer with a clog detection device, the clog detection device comprising:
a suction nozzle made of electro-conductive material configured for sucking liquid in a vessel;
a pipe connecting the suction nozzle to a discharge vessel;
a first electrode coupled to the pipe;
a second electrode coupled to the pipe and disposed in between the suction nozzle and the first electrode;
a detecting unit coupled to the suction nozzle, the first electrode, and the second electrode, wherein the detecting unit is programmed to (i) detect an output signal between the first electrode and the second electrode, between the suction nozzle and the second electrode, or between the suction nozzle and the first electrode; (ii) compare the output signal to a threshold value; and (iii) output the difference between the output signal and the threshold value over time to a determination unit coupled to the detecting unit; and
the determination unit, wherein the determination unit is programmed to (i) set a preset normal determination time and a preset clogging determination time; and (ii) determine that the suction nozzle is clogged when a totalizing time, for which the output signal exceeds the threshold value during the preset clogging determination time, is longer than a totalizing time, for which the output signal exceeds the threshold value during the preset normal determination time.

18. The analyzer of claim 17, wherein the detecting unit is programmed to output the difference between the output signal and the threshold value over time in a waveform.

19. The analyzer of claim 17, wherein the clog detection device is part of a cleaning device of an immunoassay analyzer, and wherein the cleaning device is configured to remove material not coupled to a solid phase.

20. The clog detection device of claim 1, wherein the detecting unit is programmed to detect the output signal corresponding to change of electrostatic capacitance between the first electrode and second electrode, between the suction nozzle and the second electrode, or between the suction nozzle and the first electrode.

* * * * *